United States Patent [19]

Pitt

[11] 4,064,893
[45] Dec. 27, 1977

[54] DISCHARGE SYSTEM FOR BALLAST TANK OR THE LIKE

[75] Inventor: Gillies D. Pitt, Harlow, England

[73] Assignee: International Standard Electric Corporation, New York, N.Y.

[21] Appl. No.: 745,059

[22] Filed: Nov. 26, 1976

[30] Foreign Application Priority Data

Dec. 4, 1975 United Kingdom ............... 49822/75

[51] Int. Cl.² ............................................ G05D 11/00
[52] U.S. Cl. .................................... 137/115; 137/119; 210/83; 210/96 R

[58] Field of Search ......................... 141/1, 83, 94–96, 141/192, 217, 392; 137/119, 115, 172; 73/61.1 R; 210/83, 96 R

[56] References Cited

U.S. PATENT DOCUMENTS 3,253,711 5/1966 Young ............................. 137/172 X
3,559,670 2/1971 Yedidiah ......................... 137/119 X Primary Examiner—Richard E. Aegerter
Assistant Examiner—Frederick R. Schmidt
Attorney, Agent, or Firm—A. Donald Stolzy

[57] ABSTRACT

A protection system for directing high oil content water ballast discharge to a slop tank and for controlling the rate of discharge of low oil content water ballast.

1 Claim, 1 Drawing Figure

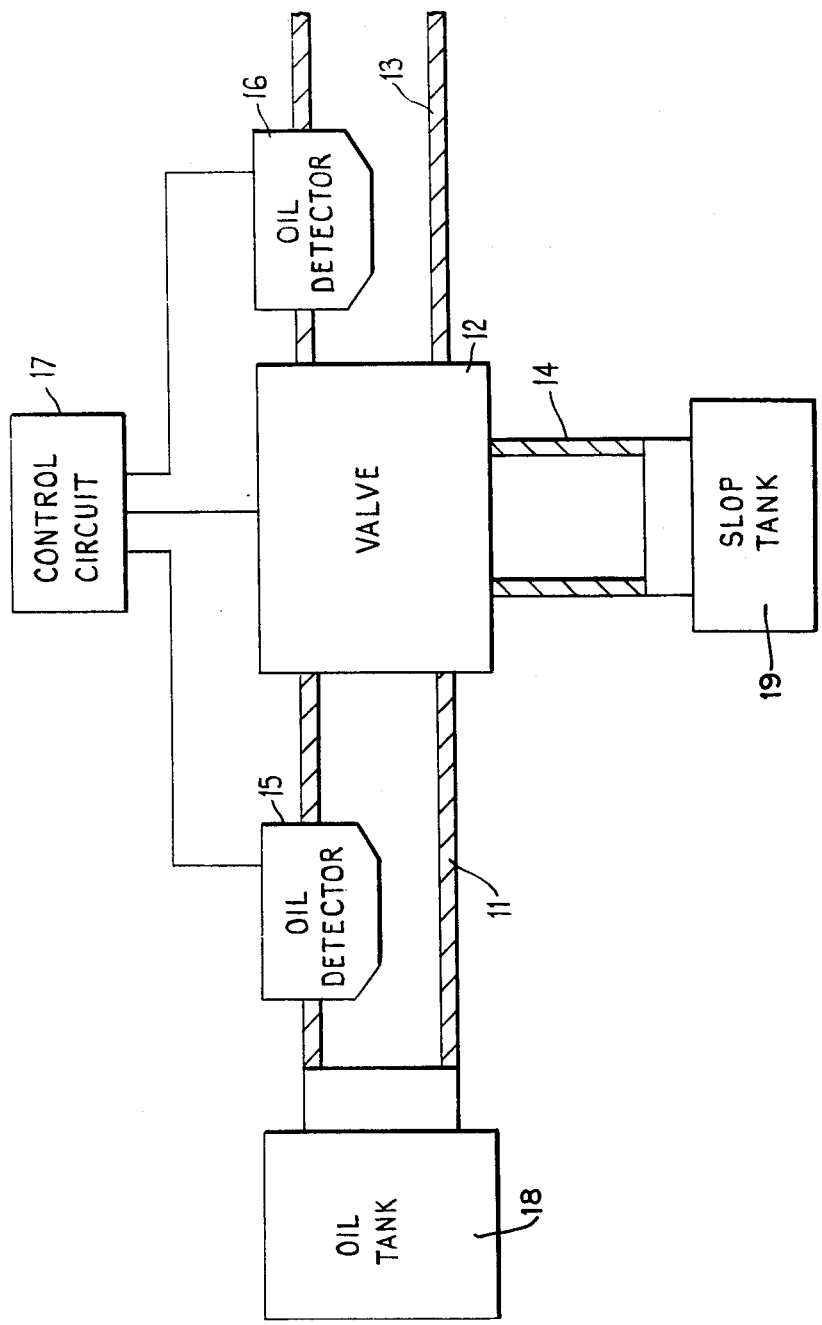

DISCHARGE SYSTEM FOR BALLAST TANK OR THE LIKE

BACKGROUND OF THE INVENTION

This invention relates to oil in water detector arrangements, and in particular to a detector/control system for discharge of water and oil from a water ballast tank.

A major problem with oil in water detectors for on-line detection and measurement of oil in the ballast water discharge of an oil tanker is that, when the discharge has either a high oil content or consists entirely of crude oil, the highly accurate optical techniques which are used to measure small quantities of oil are rendered ineffective either because of window staining or, in the case of ultraviolet fluorescence measurement, by swamping the detector.

SUMMARY OF THE INVENTION

In accordance with the arrangement of the present invention, the above-described and other disadvantages of the prior art are overcome by providing a discharge system for a tank containing an oil and water mixture, said system comprising: an oil tank; a valve having an inlet and first and second outlets; a first conduit connected between said oil tank and said valve inlet; a first detector having an output lead, said first detector being constructed to produce an output signal on said output lead thereof in accordance with the amount of oil present within said first conduit; a control circuit connected from said first detector to said valve; a slop tank; and a second conduit connected from said first valve outlet to said slop tank, said control circuit causing the fluid in said first conduit to pass through one of said first and second valve outlets, depending upon whether or not the oil within said first conduit is above a first predetermined threshold level.

The above-described and other advantages of the present invention will be better understood from the following detailed description when considered in connection with the accompanying drawing.

BRIEF DESCRIPTION OF THE DRAWING

In the drawing which is to be regarded as merely illustrative:

The FIGURE is a diagrammatic view of an oil and water discharge system.

DESCRIPTION OF THE PREFERRED EMBODIMENT

According to the invention there is provided an arrangement adapted to control the discharge of oil contaminated ballast water from an oil tank, including a discharge pipe for carrying the water from the tank, a two-way valve in said discharge pipe leading to a branch waste recovery pipe, a relatively low sensitivity oil in water detector located in said discharge pipe between the tank and the two-way valve and a control circuit connected to the output of the coarse detector and adapted to operate the two-way valve, in which, when the oil contamination of water discharging from the tank is less than the threshold of the detector the control circuit operates the valve so as to allow the water to discharge along the discharge pipe, and in which, when the oil contamination of water discharging from the tank is greater than the threshold of the detector, an output is fed to the control circuit which circuit operates the valve so as to divert the water to the waste recovery pipe.

According to the invention there is further provided an arrangement adapted to control the discharge of water ballast from an oil tank of a seagoing vessel, including a discharge pipe for receiving water discharged from the tank, a branch waste recovery pipe communicating with the discharge pipe via a two-way valve and leading to a slop tank, and a coarse and fine oil in water detector fitted to the discharge pipe on the tank side and the discharge side of the valve respectively, and a control circuit coupled to the outputs of the detectors and adapted to operate the valve, in which, when the oil contamination of ballast water discharging from the oil tank exceeds the threshold of the coarse detector, the coarse detection produces an output causing the control circuit to divert the discharge water via the valve and the branch pipe to the slop tank, in which, when the oil contamination of the ballast water is below the threshold of the coarse detector, the control circuit directs the water flow via the valve past the fine detector, and in which said fine detector is adapted to provide oil concentration signals to the control circuit, whereby the control circuit controls the rate of discharge of the ballast water.

Referring to the drawing, the arrangement includes a pipe 11 carrying water from an oil tank 18 and leading via a two-way valve 12 either to a discharge pipe 13 or pipe 14 leading to a slop tank 19. Oil detectors 15 and 16 are provided in the pipe 11 and the discharge pipe 13 respectively either side of the two-way valve 12. In some applications the detectors 15 and 16 may be located in branch pipes communicating with the pipes 11 and 13.

The first oil in water detector 15 is a coarse detector that responds only to relatively high concentration of oil, e.g. 400 or more parts per million. If the oil content of the ballast water discharge from the tank exceeds this value, the coarse detector 15 produces an output signal which causes a control circuit 17 to operate the two-way valve 12 so as to divert the discharge water to the slop tank 19. The detector 15 may advantageously be of the acoustic type or a net oil computer or probe therefor. If the former, it may include a piezoelectric transducer to detect density changes in the discharge flow from between about 1.00 for water and 1.03 for sea water, and around 0.96 for crude oil. Alternatively, a capacitive or conductivity detector may be employed to measure the large capacity or electrical conductivity differences between sea water and oil.

If, however, the ballast water discharge from the tank contains less than 400 parts per million of oil, i.e. it is sufficiently innocuous for controlled disposal, and does not damage the performance of the fine detectory, the two-way valve 12 allows the water to enter the discharge pipe 13 past the sensitive or fine detector 16. This detector, which may be of the ultraviolet fluorescence, infrared, white light scattering, fiber optic or other type, is capable of measuring oil concentration in water as low as 20 parts per million. The output of the detector 16 may alternatively be fed to a meter or a recording device to provide a record of the quantity or quality of oil released in the ballast water.

In a particularly advantageous embodiment, the system may be adapted to control water ballast discharge from the oil tanks of a seagoing tanker. The output of the detector 16 is fed to the control circuit 17, which may be of the type which controls the rate of water ballast release depending on such factors as the oil concentration in the water ballast, the vessel's speed, and the prevailing wave conditions.

What is claimed is:

1. A discharge system for a tank containing an oil and water mixture, said system comprising: an oil tank; a valve having an inlet and first and second outlets; a first conduit connected between said oil tank and said valve inlet; a first detector having an output lead, said first detector being fixed in said first conduit and constructed to produce a course output signal on said output lead thereof in accordance with the amount of oil present within said first conduit; a control circuit having a first lead connected from said first detector output lead, and a second lead connected to said valve; a slop tank; and a second conduit connected from said first valve outlet to said slop tank, said control circuit causing the fluid in said first conduit to pass through said first valve outlet when the oil within said first conduit is above a first predetermined threshold level wherein a third conduit is connected from said second valve outlet, a second detector having an output lead connected to said control circuit, said second detector being mounted within said third conduit to produce a fine output signal on said output lead thereof in accordance with the amount of oil present within said third conduit, said control circuit controlling the rate of discharge through said third conduit, said second detector being more sensitive than said first detector.

* * * * *